United States Patent
Schick

(12) 
(10) Patent No.: US 6,729,350 B2
(45) Date of Patent: May 4, 2004

(54) VALVE FOR USE WITH CAPILLARY TUBING

(75) Inventor: Hans G. Schick, Concrete, WA (US)

(73) Assignee: Upchurch Scientific, Inc., Oak Harbor, WA (US)

( * ) Notice: Subject to any disclaimer, the term of this patent is extended or adjusted under 35 U.S.C. 154(b) by 95 days.

(21) Appl. No.: 10/154,879

(22) Filed: May 24, 2002

(65) Prior Publication Data
US 2002/0195150 A1 Dec. 26, 2002

Related U.S. Application Data
(60) Provisional application No. 60/293,654, filed on May 25, 2001.

(51) Int. Cl.[7] .............................................. F16K 11/074
(52) U.S. Cl. .................................................. 137/625.46
(58) Field of Search ...................... 137/625.46; 422/103

(56) References Cited

U.S. PATENT DOCUMENTS 3,752,167 A * 8/1973 Makabe ................. 137/625.41
4,182,184 A * 1/1980 Bakalyar et al. ......... 73/864.87
4,242,909 A * 1/1981 Gundelfinger ........... 73/864.21
4,792,396 A * 12/1988 Gundelfinger ........... 210/198.2
5,419,208 A * 5/1995 Schick ..................... 73/863.73
5,482,628 A * 1/1996 Schick ..................... 210/198.2
5,863,428 A * 1/1999 Ma et al. .................. 210/198.2
6,267,930 B1 * 7/2001 Ruediger et al. ........... 422/130
6,311,719 B1 * 11/2001 Hill et al. .................... 137/312
6,390,127 B2 * 5/2002 Schick ................... 137/625.46

* cited by examiner

Primary Examiner—John Fox
(74) Attorney, Agent, or Firm—Vinson & Elkins L.L.P.

(57) ABSTRACT

A multi-port valve useful in chromatography or other analytical chemistry processes utilizes a ferrule and clamp assembly to connect a number of tubes or capillaries to a common port in the valve. The use of the clamping assembly, as opposed to conventional connectors such as nuts and/or bolts, permits the capillary ends to be positioned in extremely close proximity to the valve rotor and to each other, thus minimizing the volume between two capillaries when they are in brought into fluid communication with each other. At the same time, the clamps allow for easier connection and disconnection of the tubes or capillaries from the valve body. An operator can twist a screw to tighten the clamp and create a sealed connection without the need for special tools.

19 Claims, 9 Drawing Sheets

VALVE FOR USE WITH CAPILLARY TUBING

CROSS-REFERENCE TO RELATED APPLICATIONS

This application claims priority to U.S. provisional patent application Ser. No. 60/293,654, filed May 25, 2001.

FIELD OF THE INVENTION

This invention relates to a multi-port valve that is used for selection of fluid streams and/or injection of fluids in processes such as liquid chromatography and mass spectrometry. In particular, the invention relates to an injection/selection valve that utilizes a clamping assembly to connect tubes or capillaries to a common port in the valve with minimal dead volume.

BACKGROUND OF THE INVENTION

Multiport selector/injector valves are well known and have been used in a variety of industrial processes, such as liquid chromatography and mass spectrometry. For example, selection valves are commonly used in liquid chromatography and other analytical methods to direct fluid flow along alternate paths. Such valves are also used to terminate fluid withdrawal from one source and select another source of fluid, for example, such as when a variety of streams in an industrial process is selectively sampled for analysis.

Injector/selector valves are often used in high pressure liquid chromatography (HPLC) or gas chromatography (GC). U.S. Pat. No. 4,242,909 (Gundelfinger '909), which is hereby fully incorporated by reference, describes a sample injection apparatus for withdrawing liquid samples from vials and injecting them into a chromatographic column or other analyzing device. The apparatus is said to minimize wastage, cross contamination, and dilution of the samples, and to be capable of automation with a minimum of complexity. Injector/selector valves are particularly useful in chromatographic applications since a substantial amount of time and effort is required to set up a particular HPLC or GC system, which may often utilize multiple columns and/or multiple detection systems. Multiport selection valves permit the operator of the chromatograph to redirect flows such that particular samples are selected for injection into a particular column, or alternatively, to direct the output from a particular column to one or more different detectors.

As mentioned above, multiport selection valves have been known for some time, including those which utilize a cylindrical rotor and stator combination. In some of these valves, the stator holds the fluid tubes in fixed relation to each other and presents the tube ends to a rotor face which may contain a grooved surface. By varying the angle of the rotor, the tubes are selectively brought into fluid communication. One type of injector/selector valve using a rotor/stator combination is the Type 50 rotary valve from Rheodyne, Incorporated. The Type 50 valves are said to operate by rotation of a flat rotor against a flat stator (see "Operating Instructions for Type 50 Teflon Rotary Valves," Rheodyne, Incorporated, printed in U.S.A. April 1994). Another rotor/stator selector valve is shown in U.S. Pat. No. 5,193,581 (Shiroto, et al.), which is hereby fully incorporated by reference. The valve is said to comprise, among other things, a stator plate having a plurality of outlet holes extending through the stator plate and arranged in a circle concentric with a valve casing, and a rotor having a U-shaped passage formed in the rotor. The rotor is said to be rotated through a desired angle so that an inlet hole can be in fluid communication with selected ones of the outlet holes through the U-shaped passage of the rotor.

U.S. Pat. No. 5,419,419 (Macpherson) describes a rotary selector valve that is used in connection with an automatic transmission in an automobile. A motor is said to index a shear plate of the selector valve to predetermined positions for shifting the transmission. A series of working lines as shown in FIG. 6 are maintained in a closed spatial relationship with the casing.

U.S. Pat. No. 3,494,175 (Cusick, et al.) discloses a valve having a plurality of capillaries which are held in spaced relationship within a manifold plate member. U.S. Pat. No. 3,752,167 (Makabe) discloses a fluid switching device including a plurality of capillaries that are held within threaded holes by couplings. A rotary member allows fluid communication between the tubes. U.S. Pat. No. 3,868,970 (Ayers, et al.) discloses a multipositional selector valve said to be adapted with a means for attaching a plurality of chromatographic columns to the valve, such that the flow can be directed into any of the columns. U.S. Pat. No. 4,705,627 (Miwa, et al.) discloses a rotary valve said to consist of two stator discs and a rotor disposed between the two stator discs. Each time the rotor is turned intermittently it is said, different passages are formed through which the fluid in the valve runs. U.S. Pat. No. 4,722,830 (Urie, et al.) discloses multiport valves. The multiport valves are said to be used in extracting fluid samples from sample loops connected with various process streams.

In many applications using selector/injector valves to direct fluid flows, and in particular in liquid and gas chromatography, the volume of fluids is small. This is particularly true when liquid or gas chromatography is being used as an analytical method as opposed to a preparative method. Such methods often use capillary columns and are generally referred to as capillary chromatography. In capillary chromatography, both gas phase and liquid phase, it is often desired to minimize the internal volume of the selector or injector valve. One reason for this is that a valve having a large volume will contain a relatively large volume of liquid, and when a sample is injected into the valve the sample will be diluted, decreasing the resolution and sensitivity of the analytical method.

In the design of selector or injector valves with minimal internal volume, the prime design consideration is to bring all of the fluid passages into the closest possible proximity to each other. To do this with conventional capillary connectors is very difficult, since the nuts of the connectors are relatively large and require a fair amount of space. Thus, the valve itself has to be relatively large in order to accommodate the connections.

One solution to the large connectors has been to drill the injector ports on an angle. By angling the injector ports, the ends of the channels can all emerge in close proximity to a common point, while the opposite ends of the channels are sufficiently spaced apart to accommodate the larger connectors. An example of this approach is shown in U.S. Pat. No. 5,419,208 (Schick), which is hereby fully incorporated by reference. However, this approach has certain drawbacks. First, angled holes are difficult to produce and expensive to machine. Further, the angled passage from the capillary connector to the center of the valve stator is longer than it would be if the capillary could be connected directly on the face of the valve in close proximity to other capillaries. This additional length creates additional dead volume, which is undesirable as noted above. A further disadvantage of this approach is that the emerging hole near the center of the valve stator has an elliptical shape, which is not desirable.

Another type of capillary connection is shown in U.S. Pat. No. 4,792,396 (Gundelfinger '396), which is hereby fully incorporated by reference. Gundelfinger '396 describes a frame used as part of an injector said to be useful in loading a sample at high pressure into a chromatographic column. The frame is said to comprise ferrules for sealing tubes, and it is said that a tube coupling hole in the frame can couple to a standard 1/16" tube, but also can couple to a much smaller diameter tube useful for minimizing dispersion when small samples or small chromatographic columns are used. The use of ferrules to make capillary or tubing connections to chromatography apparatus is also shown in, for example, U.S. Pat. Nos. 5,674,388 (Anahara), 5,744,100 (Krstanovic), 5,472,598 (Schick), 5,482,628 (Schick), and 5,366,620 (Schick).

Still another approach involves the use of "ferrule clusters," as described and explained in my copending U.S. patent application Ser. No. 09/343,131, titled "Selection Valve with Ferrule Cluster," which is hereby fully incorporated by reference. The ferrule clusters minimize dead volume, but require the connection (or disconnection, as the case may be) of two or more capillaries to (or from) the valve at a time.

It would be desirable to have a selector/injector valve that can be made with the smallest possible valve volume. There is also a need for an injector/selector valve which brings capillary or tube ends into the closest possible proximity to each other and to the valve stator so that valve dead volume is minimized. There is also a need for a capillary connector system that can be used to connect capillaries in the closest possible proximity. Moreover, there is a need for apparatus and methods which allow an operator greater flexibility in selectively connecting and/or disconnecting capillaries to a valve while still meeting the other objectives.

SUMMARY OF THE INVENTION

The invention relates to a multi-port injection/selection valve that utilizes a clamp and ferrule assembly configuration to connect tubes or capillaries to a common port, or to each other, in the valve. The clamp and ferrule assemblies connect the tubes or capillaries to the body of the valve assembly. The use of the individual clamp and ferrule assemblies, as opposed to conventional connectors, permits the capillary ends to be positioned in extremely close proximity to the valve rotor and to each other, thus minimizing the space between two capillaries when they are in brought into fluid communication with each other (often referred to as the "dead volume" in the connection). The clamp and ferrule assemblies of the present invention also allow an operator to connect, or disconnect, one or more capillaries without connecting, or disconnecting the other capillary connections to the valve.

In one embodiment the invention is a valve, comprising: a) a plurality of clamp and ferrule assemblies, each having a ferrule and a clamp for removably attaching a capillary tube to the valve; b) a stator in contact with at least one of said ferrules, said stator having a stator front side and a stator flat surface opposite said front side, said stator front side having a plurality of impressions into which some or all of said ferrules are received, each of said impressions opening to a terminal cylindrical bore (tube pocket), each of said impressions also having a stator through-hole opening onto said stator flat surface; c) a plurality of capillary tubes, each of said capillary tubes extending through at least one of said ferrules and into a stator impression up to the terminus of said cylindrical bore; and d) a rotor comprising a stator-contact surface and at least one fluid communication channel, said stator-contact surface abutting said stator flat surface and being rotatable about an axis to establish fluid communication between selected pairs of capillaries through said fluid communication channel.

In yet other embodiments of the invention, the rotor has grooves for fluid flow that are etched into a glass, quartz, or other surface via photolithographic or other similar etching techniques. In still other embodiments of the invention, the invention is a capillary chromatographic system comprising the valve of the invention. In still other embodiments the invention is a method for carrying out a chromatographic or spectrometric analysis and methods for connecting and disconnecting capillary tubes to a chromatographic or mass spectrometry system.

DETAILED DESCRIPTION

Figure 1:
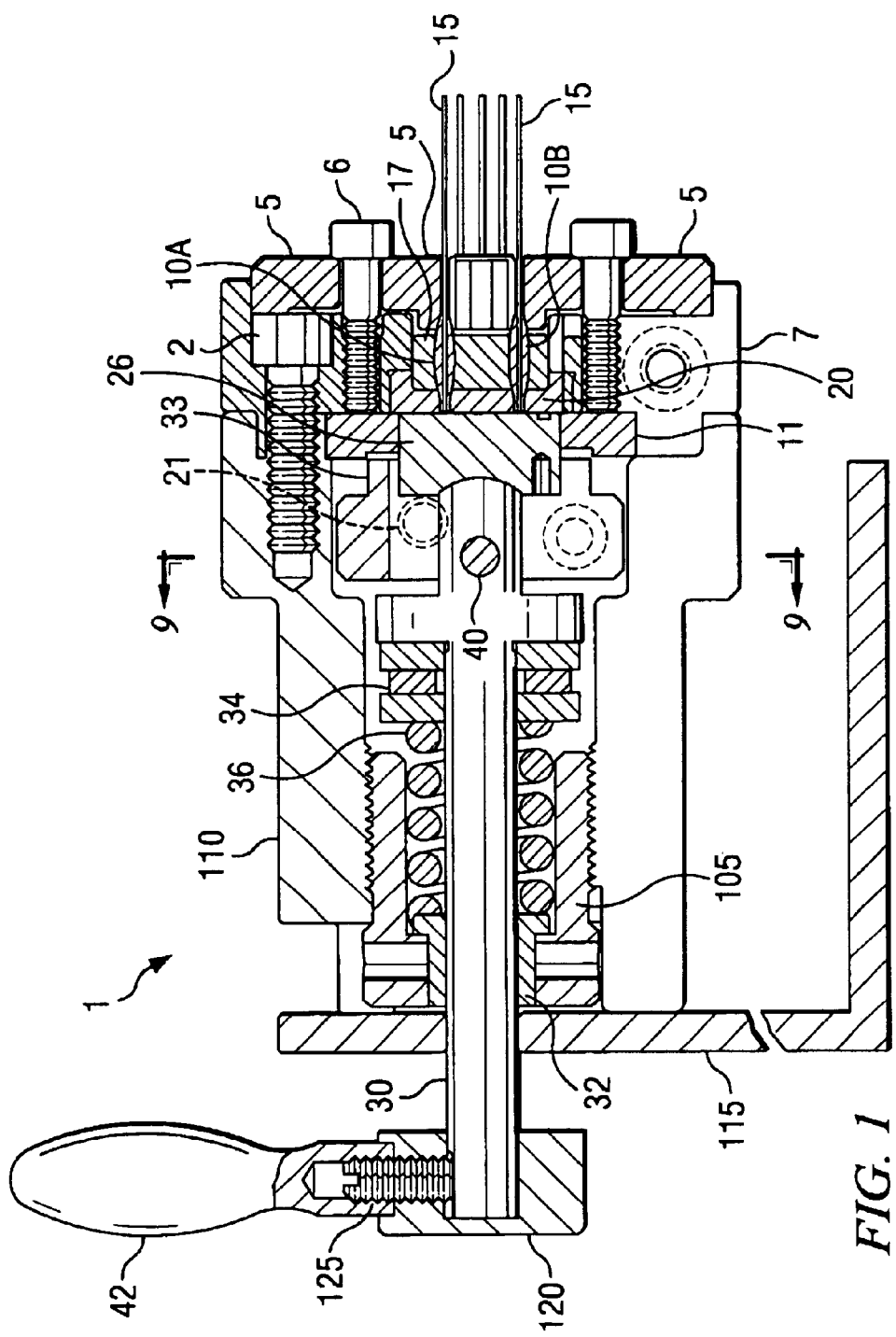
FIG. 1 is a sectional view showing a valve according to one embodiment of the invention.

As seen in FIG. 1, one embodiment of the invention comprises a valve 1 which has plurality of capillaries 15 attached with corresponding ferrules 10A and 10B. The ferrules 10A and 10B of the invention may be of the double-ended type, as shown in FIG. 1 and in FIG. 7. The double-ended type approximates two single-ended ferrules with their ends joined. Thus, the double-ended ferrules 10A and 10B each have tapered gripping portions on both of their respective ends. As shown in FIG. 1, each of the capillaries 15 extend through an opening in a corresponding clamp 5, through a corresponding ferrule 10, which itself extends through a corresponding opening in ferrule support 17, and through stator 20, such that one end of each of the capillaries 15 are in fluid communication with a front surface of rotor 26. These components of valve 1 and their various features are described below in more detail. It will be understood by those of ordinary skill that the valve 1 allows for the connection of a plurality of capillaries 15 in a manner which minimizes the dead volume between the ends of the capillaries 15, while at the same time allowing an operator to connect or disconnect one or more capillaries 15 to or from valve 10 without having to connect or disconnect all capillaries 15 at the same time.

Referring still to FIG. 1, it can be seen that valve 1 also includes a main body 110, a mounting bracket 115, a handle 42, a set screw 125 (for attaching the handle 42 to the knob 120), and a knob 120. The handle 42, set screw 125, and knob 120 are assembled and attached to one another so that, when an operator, turns handle 42, that action results in corresponding rotation of the shaft 30 and rotor 26. Those skilled in the art will understand and appreciate that handle 42 can be attached or secured to shaft 30 via other means or can be combined into a unitary item with shaft 30. Those skilled in the art will also understand and appreciate that handle 42 is useful for manual operation of the valve 1 by an operator, but the selective rotation of shaft 30 can be automated with conventional means. Those skilled in the art will further understand and appreciate the use of the adjustment nut 105 and the spring 36 to bias shaft 30 against rotor 26 to ensure that the valve 1 operates without any leaking, even at high pressures. Still referring to FIG. 1, it can be seen that each of the cap screws 6 can be tightened by an operator to bias and press the corresponding ferrule 10 and capillary 15 against the facing or abutting surface of rotor 26. This further ensures leak-free operation of the valve.

Figure 2:
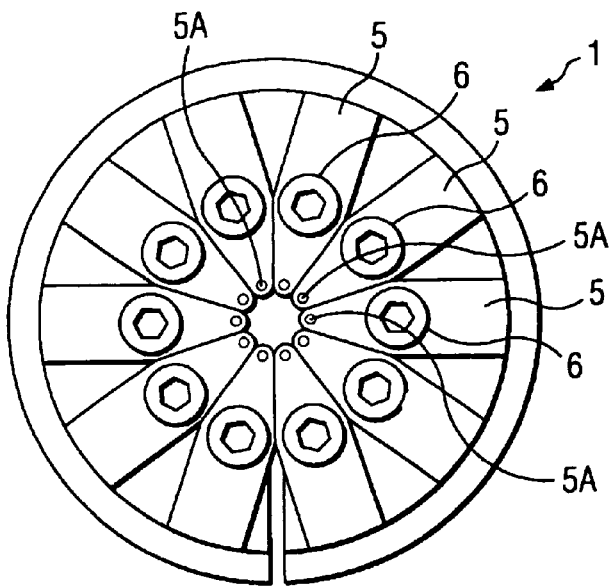
FIG. 2 shows a front view of the valve of the present invention.
Figure 9:
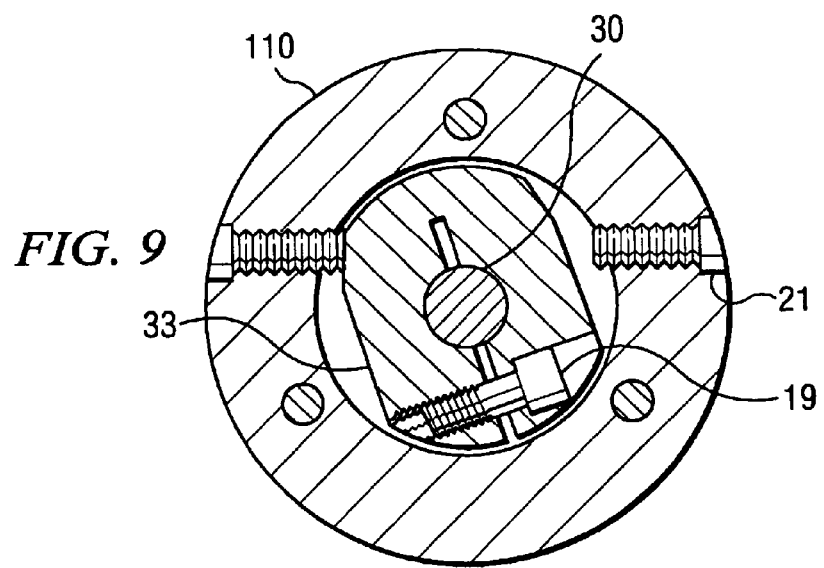
FIG. 9 is a sectional view of a valve of the present invention taken along line 9—9.

Referring now to FIG. 2, a "frontal" view of valve 1 is shown. As shown in FIG. 2, a plurality of clamps 5 are disposed on the front of valve 1. Those skilled in the art will understand that there may be more or less than ten (10) clamps 5. In FIG. 2, there are ten (10) of clamps 5. Each of clamps 5 has an opening 5a through which a capillary 15 may extend (not shown in FIG. 2). Also as shown in FIG. 2, there is a cap screw 6, a portion of which extends through the corresponding clamp 5. Those of ordinary skill will understand and appreciate that the openings 5a of clamps 5 are located in close proximity to one another, thereby minimizing the dead volume of the fluid communication between capillaries 15 when attached to valve 1 of the present invention. With the ten (10) clamps 5 configuration shown in FIG. 2, for example, I have been able to arrange the ten (10) openings 5a in a circle with a diameter of only 6 mm. As also shown in FIG. 2, the cap screws 6 (like the openings 5a) are arranged in a circle, but the diameter of the circle formed by cap screws 6 is greater than the circle arrangement of the openings 5a. This arrangement makes it easier for an operator to tighten or loosen each of the individual cap screws when connecting or disconnecting a capillary 15. While cap screws 6 are shown, those skilled in the art will understand that other screws, threaded bolts, and fastening means may be used.

Figure 3A:
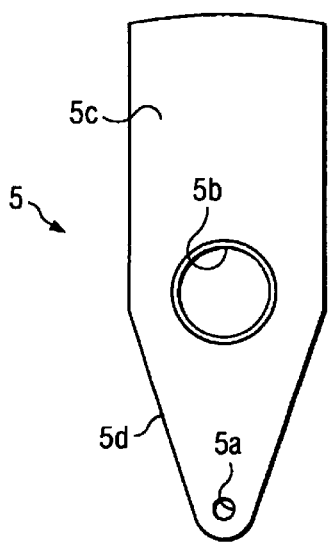
FIG. 3A shows a frontal view of a clamp in accordance with the present invention.
Figure 3B:
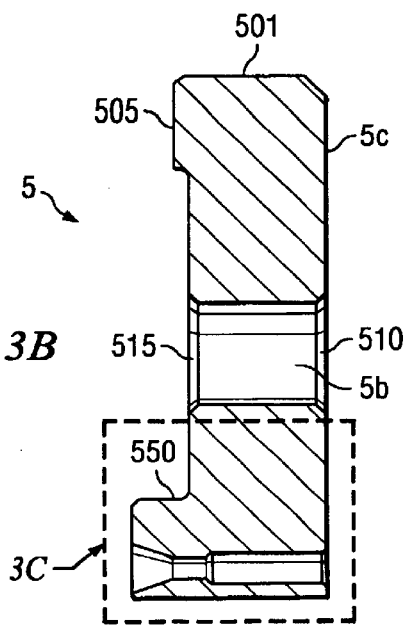
FIG. 3B shows a sectional view of the clamp shown in FIG. 3A.
Figure 3C:
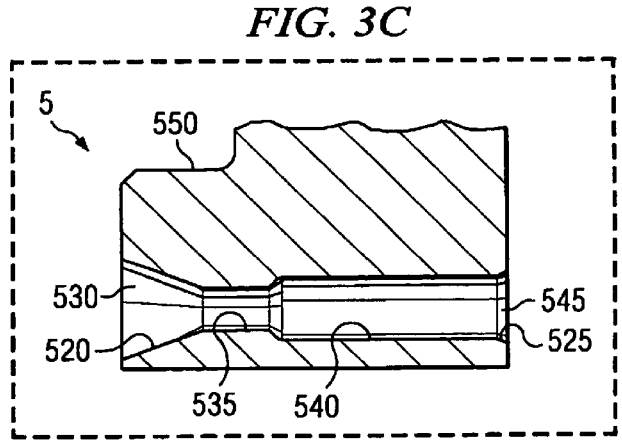
FIG. 3C shows a detailed, fragmentary sectional view of the clamp shown in FIG. 3A.

Referring now to FIGS. 3A, 3B, and 3C, a clamp 5 in accordance with the present invention is shown in greater detail. Referring first to FIG. 3A, a frontal, or overhead, view of a clamp 5 is provided. (For ease of reference, the same numbers are used in various drawings to indicate the same items or features which may be identified in other drawings.) As shown in FIG. 3A, clamp 5 has a main body 5c and also a tapered end 5d. While opening 5a may vary in size depending on the capillary 15 to be received, the valve 1 shown and described as the preferred embodiment has openings 5a which are 2 mm in diameter. The opening 5a for a capillary 15 (not shown in FIG. 3A) is located in the tapered end 5d of a clamp 5. As also shown in FIG. 3A, the clamp 5 has an opening 5b through which a portion of a cap screw 6 (not shown in FIG. 3A) may extend.

Referring now to FIG. 3B, a sectional view of a clamp 5 is provided. As shown in FIG. 3B, the main body 5c of clamp contains a back surface 501 and also an abutting surface 505. As also shown in FIG. 3B, the opening 5b includes conical surfaces 510 and 515 at each side (for convenience, the sides may be considered the "top" and "bottom" sides, respectively, of the clamp 5) the opening 5b. As also shown in FIG. 3B, the tapered end 5d of clamp 5 includes a second abutting portion 550. In addition, opening 5a includes segments or portions 530, 535, 540, and 545. As also shown in FIG. 3B, and in more detail in FIG. 3C, the opening segment 530 is conical in shape and is in direct fluid communication with segment 535. Segment 535, in turn, is in direct fluid communication with segment 540, which in turn is in direct fluid communication with segment 545, which is conical in shape. Segments 530 and 545 have tapered or conical surfaces 520 and 525, respectively. Segment 530 and conical surface 520 are adapted to receive and snugly fit one end of a ferrule 10 (as shown in FIG. 1). I prefer to have clamps 5 made of 2024 T-4 steel, but those skilled in the art will understand that other metals or suitable materials may be used instead.

Figure 4A:
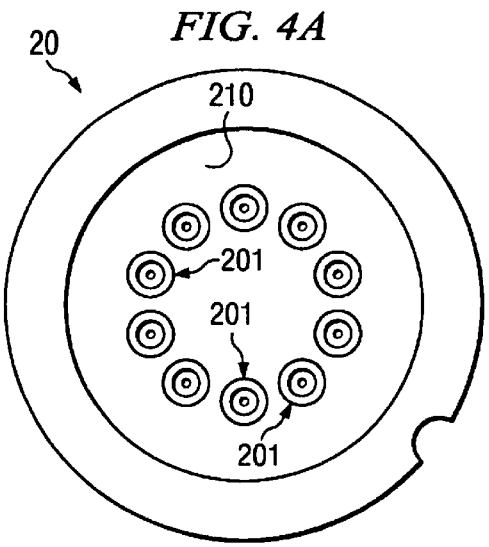
FIG. 4A shows a frontal view of a 10-port stator of a valve in accordance with the present invention.
Figure 4B:
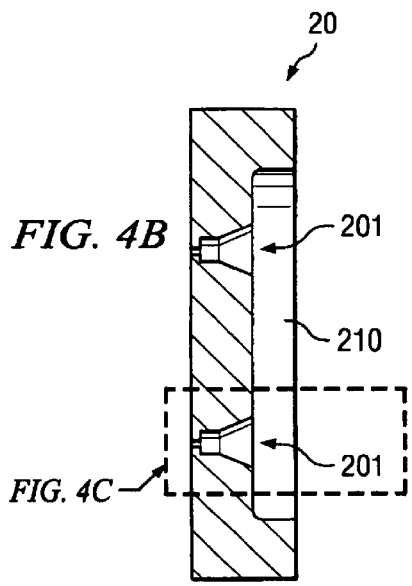
FIG. 4B shows a sectional view of the stator shown in FIG. 4A.
Figure 4C:
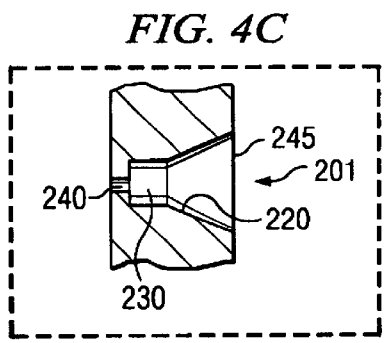
FIG. 4C shows a detailed, fragmentary, sectional view of the stator shown in FIG. 4A.

Referring now to FIGS. 4A, 4B, and 4C, additional details regarding the stator 20 of the valve 1 of the present invention are shown. Referring first to FIG. 4A, a frontal view of stator 20 is provided. As shown in FIG. 4A, the interior seat 210 of stator 20 includes ten (10) tapered openings 201. Openings 201 are arranged in a circular pattern on the surface of stator 20. Referring now to FIG. 4B, a sectional view of the stator 20 is provided. As shown in FIG. 4B, a first side of the stator 20 includes a seat 210. The seat 210 is adapted to snugly fit and hold therein at least a portion of the ferrule 17 support (as is shown in FIG. 1). Referring to FIGS. 4B and 4C, the openings 201 are shown in additional detail. As shown in FIGS. 4B and 4C, openings 201 extend through the stator 20. Openings 201 each have segments 240, 230, and 245. As shown in FIG. 4C, segment 245 is tapered and provides a conical surface 220. Segment 230 is in direct fluid communication with segment 245. Segment 240, in turn, is in direct fluid communication with segment 230. Segment 245 and conical surface 220 are adapted to receive and snugly fit a ferrule 10 with a capillary 15 located therein (as is shown in FIG. 1). Segment 230 is adapted to receive and snugly fit a portion of a capillary 15 which may extend from a ferrule. For best results, I prefer that stator 20 be made of zirconia, although other suitable materials may be used.

Referring again to FIG. 1, the capillary tubes 15 emerge from the ferrule through-holes 5a and extend up to the stator 20 through-holes 201 so that the ends of the capillaries 15 are, as noted above, substantially flush with the terminus of a tube pocket. The capillary ends disposed in the tube pockets are naturally in the same relative positions in which the ferrules 10 are arranged. That is, the capillary ends are distributed on the stator 20 evenly around the circumference of a circle.

Figure 5A:
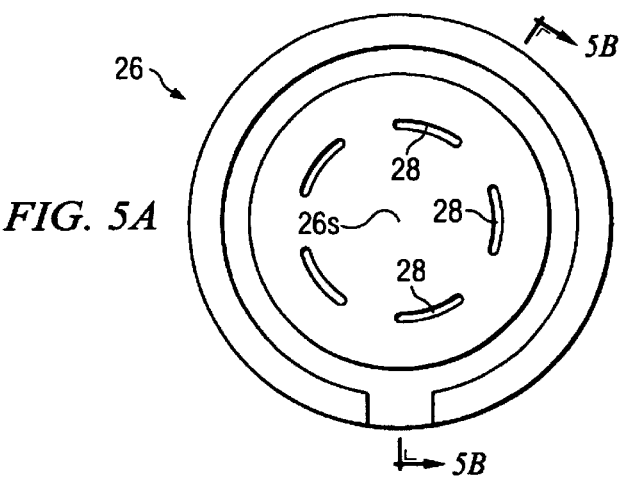
FIG. 5A shows a frontal view of a 10-port rotor of a valve in accordance with the present invention.
Figure 5B:
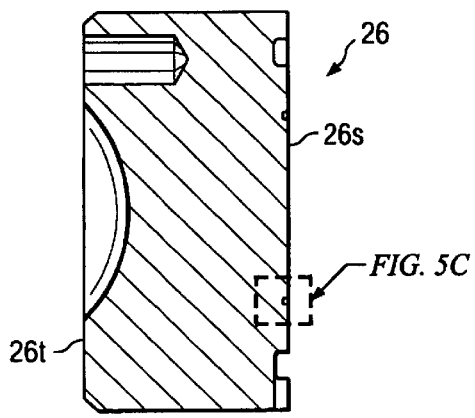
FIG. 5B shows a sectional view of the rotor shown in FIG. 5A.

Referring once more to FIG. 1, the valve 1 shown therein comprises a rotor 26 which abuts the stator 20. The rotor 26 may be of any number of types. Referring to FIGS. 5A and 5B, the rotor 26 shown therein has a grooved stator contact surface 26s and a rotor shaft contact surface 26t. Grooves 28 are formed in the stator contact surface 26s. As shown in FIG. 1, the rotor contact surface 26s abuts one side of the stator 20. Continuing to refer to FIG. 1, the rotor shaft contact surface 26t is connected to a rotor shaft 30 for varying the angle of the rotor 26 with respect to the stator 20. By rotating the rotor surface 26s, the rotor groove(s) 28 may be selectively positioned to establish fluid communication between specific pairs of capillaries 15. Although not shown, those skilled in the art will understand and appreciate that a center capillary can be used and, if so, the grooves 28 can be formed to allow movement of the rotor 26 to selectively provide fluid communication between the center capillary and one or more of the other capillaries. The rotor 26 shown in FIGS. 5A, 5B, and 5C may be used when it is desired to establish fluid communication between various pairs of the capillaries 15. I prefer to use a rotor 26 made of zirconia, but those skilled in the art will understand and appreciate that other suitable materials may be used.

Figure 5C:
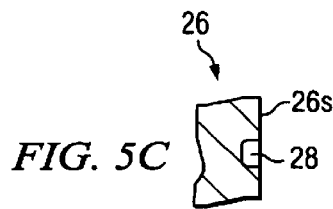
FIG. 5C shows a detailed, enlarged sectional view of a portion of the rotor shown in FIGS. 5A and 5B.

While the rotor 26 shown in FIGS. 5A, 5B, and 5C use grooves 28 cut into the rotor surfaces to permit fluid communication between various capillary 15, any type of fluid communication channel could be provided on the rotor 26. For example, rather than grooves 28, a channel could be cut in the body of the rotor 26 so that it has one opening at the center of the rotor and another opening lying along the circle circumference. However, to minimize the dead volume of the valve, grooves 28 cut into the surface of the rotor 26 are preferred as rotor fluid communication channels.

The grooves 28 on surface 26s of the rotor 26 can be formed by conventional machining techniques. Alternatively, grooves 28 can be formed by etching of a photolithography mask (photomask). According to this embodiment of the invention, a thin film (or films) is deposited on one face of the surface 26s of the rotor 26 using conventional techniques. The substrate is then coated with a suitable photoresist, is then exposed using the photomask, and is developed with a suitable developer. This process removes the photoresist from those areas of the substrate which correspond to the desired shape and arrangement of grooves 28. The substrate is then subjected to a series of steps which remove the masking material not protected by the photoresist, thus exposing the substrate in these areas. A second series of steps is then use to etch the expose substrate to etch the grooves 28 in the substrate. Because the etching process can be carefully controlled to a very high degree of precision, grooves 28 can be created to match very precise size, volume, shape, or other requirements. Moreover, by carefully controlling the size and shape of the grooves 28, the amount of dead volume can be both minimized and accurately measured, thus giving the operator more information to help design and run accurate analyses, such as by chromatography or mass spectrometry.

After the etching process is completed, the photoresist and masking layers are removed. At this point, the substrate can be coated with a thin conforming film (or films) selected to obtain the desired chemical and/or physical properties of the substrate surface. For example, a thin diamond-like coating can be applied to increase the surface hardness. Those skilled in the art will understand and appreciate that, depending on the solvents used, the materials being analyzed, and other various parameters, the ability to select desired chemical and/or physical properties (such as hardness, resistance to corrosion, extremely smooth surfaces, and so forth) will provide many advantages. In addition, a precision saw can be used to cut the substrate into individual pieces for rotor 26, thus allowing a high degree of precision in the alignment and location of grooves 28 on surface 26s of rotor 26.

Figure 5D:
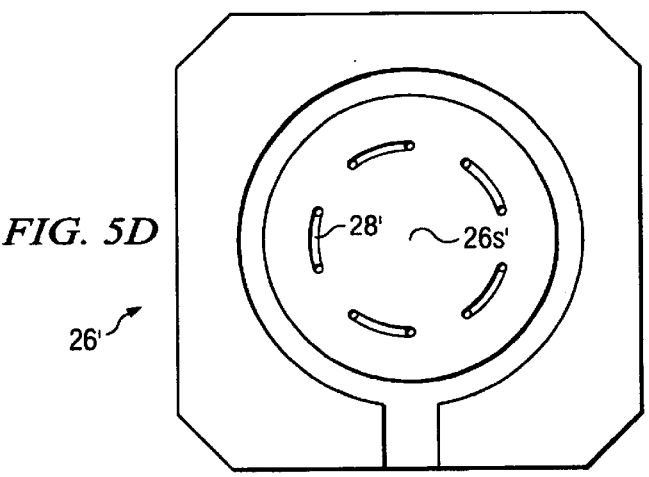
FIGS. 5D, 5E, and 5F show a frontal view, sectional view, and rear view, respectively, of an alternative embodiment of a rotor of a valve in accordance with the invention.
Figure 5F:
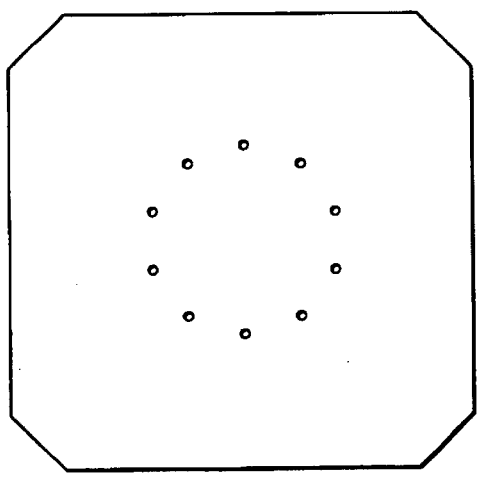
Figure 5E:

Referring now to FIGS. 5D, 5E, and 5F, an alternative embodiment of a rotor 26' is shown. Rotor 26' has a plurality of grooves 28' in a first surface thereof. Grooves 28' allow for selected fluid communication between the ports of the rotor 26'.

Figure 6A:
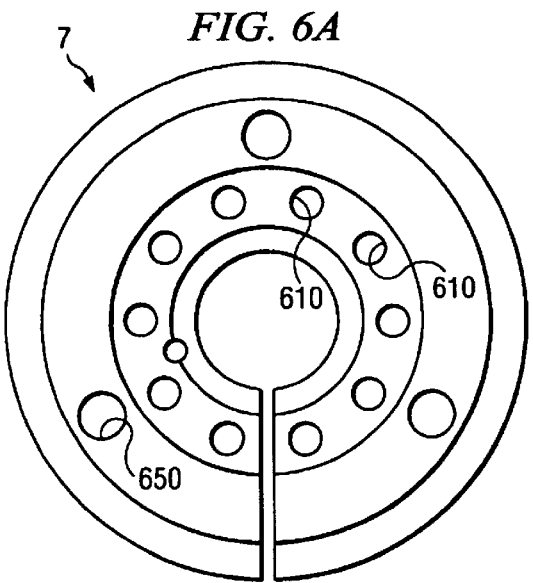
FIG. 6A shows a frontal view of a 10-port stator plate in a valve in accordance with the present invention.
Figure 6B:
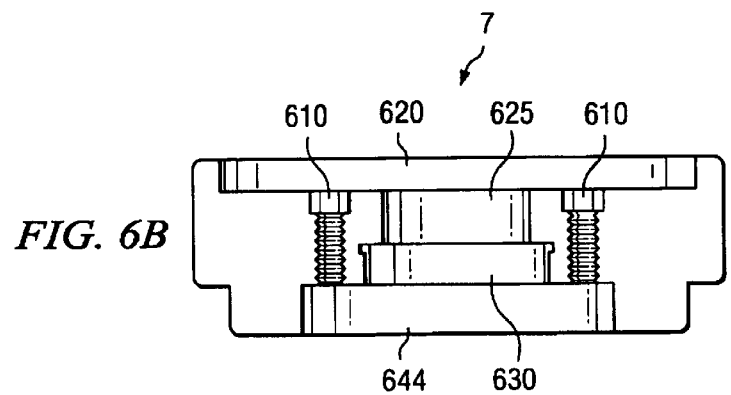
FIG. 6B shows a sectional view of the stator plate shown in FIG. 6A.

Referring now to FIGS. 6A and 6B, additional detail regarding the stator plate 7 is provided. In FIG. 6A, a frontal view of stator plate 7 is provided, while in FIG. 6B a sectional view is provided. As shown in FIG. 6A, the stator plate 7 contains ten (10) openings 610, which are arranged in a circle. The openings 610 are adapted to receive the cap screws 6 which are used to secure the corresponding clamps 5 (as shown in FIG. 1). Stator plate 7 also includes openings 650 for receiving cap screws 2 to firmly (albeit removably) secure stator plate 7 to one end of the main body 110 of valve 1 (as shown in FIG. 1). As shown in FIG. 6A, the stator plate 7 has three (3) openings 650 for receiving cap screws 2. As shown in FIG. 6B, stator plate 7 has central opening segments 620, 625, 630, and 644. In addition, openings 610 have treaded portions for receiving and removably securing cap screws 6 (as shown in FIG. 1). Segments 620 and 625 are adapted for receiving abutting portions of clamps 5, ferrule support 17, and stator 20 (as shown in FIG. 1). Segment 644 is adapted to fit and receive sleeve bearing 11 (as shown in FIG. 1). For best results, I prefer that stator plate 7 be made of 316 stainless steel, although other metals and other suitable materials may be used instead.

Figure 7:
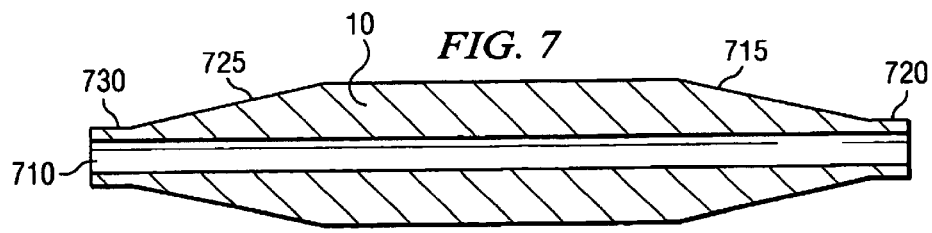
FIG. 7 shows a ferrule in accordance with the present invention.

Referring now to FIG. 7, a cross section of a ferrule 10 is provided. As shown in FIG. 7, the ferrule 10 has a through-hole 710 extending through its length. The opening 710 is adapted to receive a capillary 15. As shown in FIG. 7, ferrule 10 is symmetric and has opposing ends 720 and 730. Referring to FIG. 1, it can be seen that ends 720 and 730 are adapted to fit into openings in the stator 20 and the clamp 5. (Because the ferrule 10 is symmetric, either end 720 or 730 will fit into the respective openings of stator 20 and clamp 5.) As also shown in FIG. 7, ferrule 10 has tapered portions 752 and 715. The tapered portions 725 and 715 are adapted to fit into conical openings in stator 20 and clamp 5 (as shown in FIG. 1). For best results, I prefer to use ferrules 10 made of polyether-ether ketone (PEEK), which is commercially available.

Figure 8A:
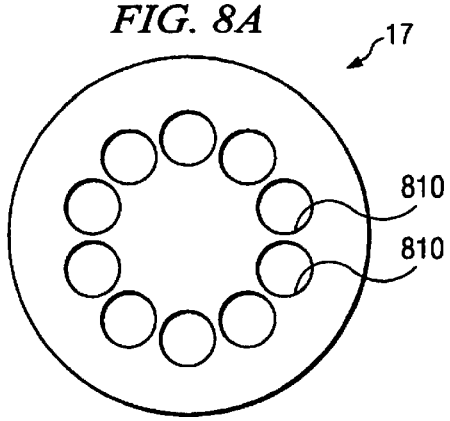
FIG. 8A shows a frontal view of a ferrule support in a valve in accordance with the present invention.
Figure 8B:
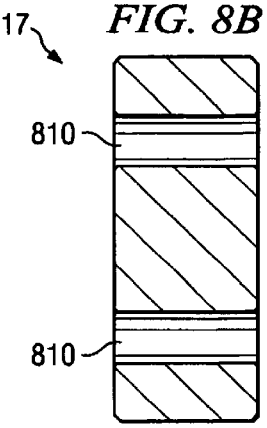
FIG. 8B shows a sectional view of the ferrule support shown in FIG. 8A.
Figure 10A:
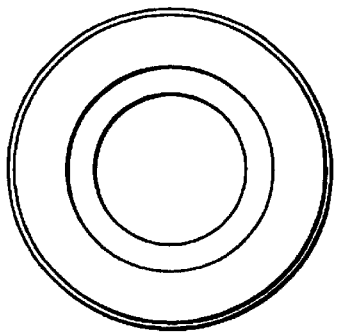
FIGS. 10A, 10B and 10C are, respectively, a frontal view, sectional view, and sectional view along line 10A—10A, of an adjustment nut in a valve of the present invention.
Figure 10B:
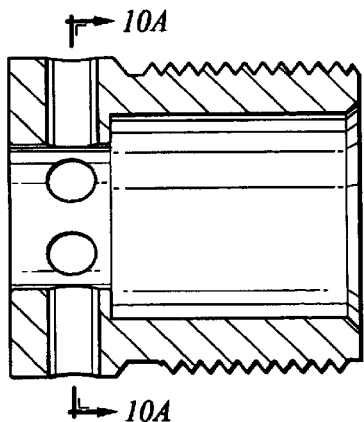
Figure 10C:
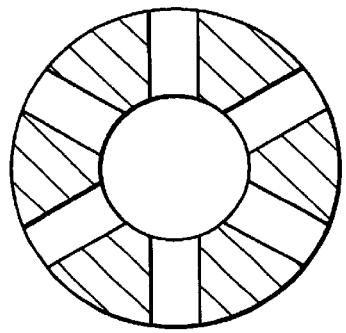
Figure 11A:
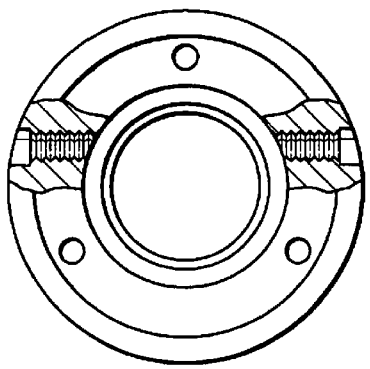
FIGS. 11A, 11B, and 11C are a frontal view, sectional view, and rear view, respectively, of the main body of a valve of the present invention.
Figure 11B:
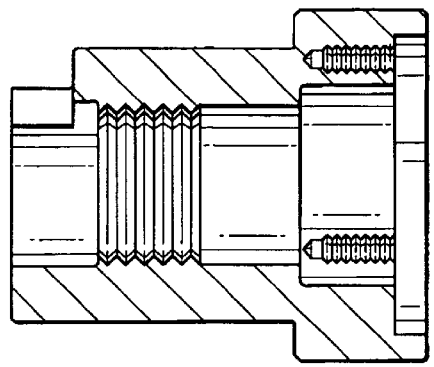
Figure 11C:
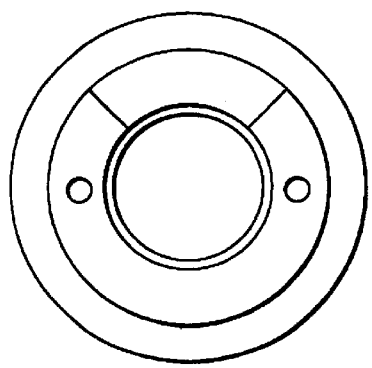
Figure 12A:
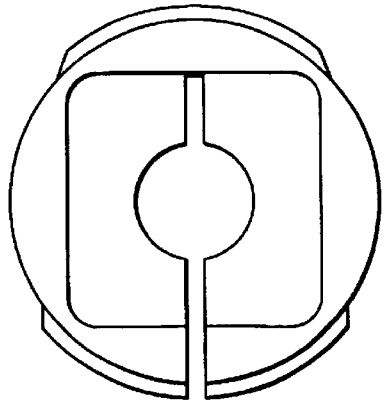
FIGS. 12A, 12B, and 12C are a frontal view, sectional view, and rear view, respectively, of the rotor mount of a valve of the present invention.
Figure 12B:
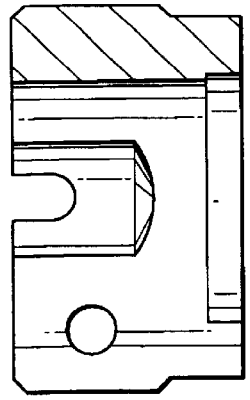
Figure 13A:
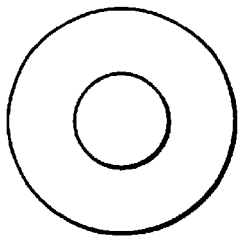
FIGS. 13A and 13B are a frontal view and a side view, respectively, of a drive shaft of a valve of the present invention.
Figure 12C:
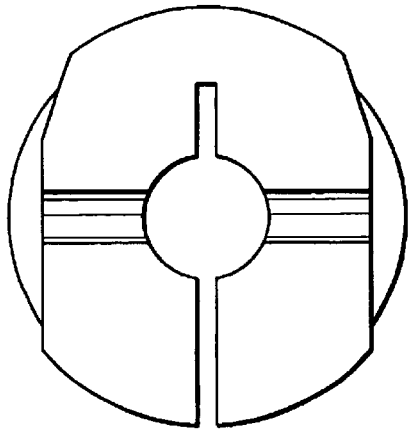
Figure 13B:
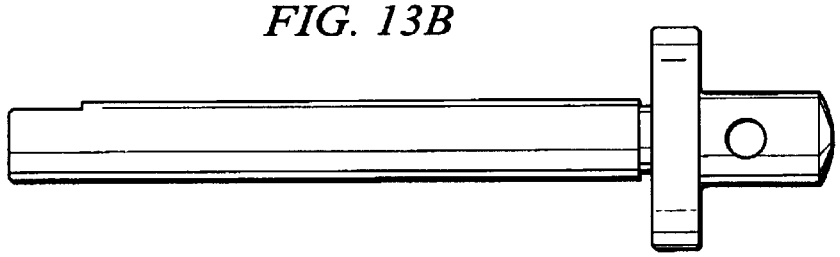
Figure 14A:
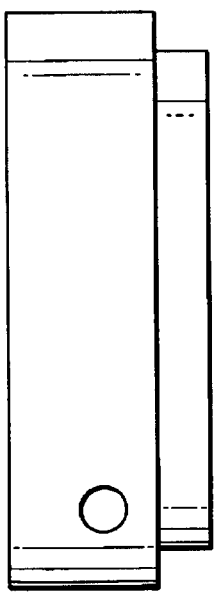
FIGS. 14A and 14B are side and frontal views, respectively, of an alternative stator plate of a valve in accordance with the present invention.
Figure 14B:
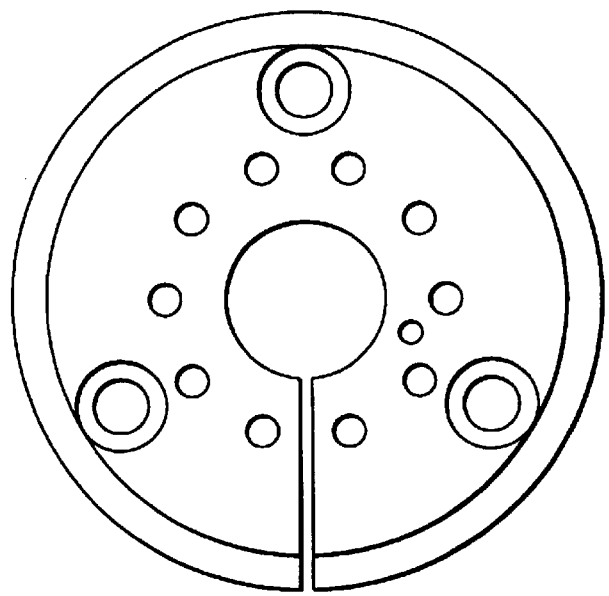

Referring now to FIGS. 8A and 8B, the ferrule support 17 is shown in additional detail. As shown in FIGS. 8A and 8B, the ferrule support 17 has ten (10) openings 810, which are generally located in a circle. The openings 810 are adapted to receive and snugly fit ferrules 10 (as shown in FIG. 1). I prefer to have a ferrule support 17 made of PEEK, but any suitable material may be used.

Returning to FIG. 1, rotor shaft 30 is connected to rotor surface 26*t* and is supported by bearing bushing 32 and roller thrust bearing 34. A spring 36 is used to bias the rotor shaft and rotor 26 toward the stator 20. A rotor driver pin 40 engages the rotor, and a handle 42 is used for operating the rotor if manual rotation thereof is desired. Obviously, any number of automatic means for rotating the rotor could be connected to the rotor shaft.

The various components of valve 1 as described above may be fabricated form any suitable material, including thermoset materials and thermoplastics. Polyether-ether ketone (PEEK) is a particularly suitable thermoplastic material for fabricating the ferrules of the invention. The rotor and stator of the inventive valve may be fabricated from any suitable material, for example, metal, plastic materials, ceramic materials, or zirconia. In a preferred embodiment, the rotor and stator are ceramic or zirconia.

The valve of the instant invention may be fabricated to any useful size. However, the inventive valve is particularly useful in micro applications, in particular those utilizing fluid flow rates of 0.5 ml/min or less. For example, in the preferred embodiment shown above, the valve 1 is able to selectively connect ten (10) capillaries 15 with a port to port distance of 2 mm arranged in a circle with a diameter of 6 mm. The valve 1 of the present invention thus minimizes dead volume while providing a great deal of flexibility and ease of use to an operator because each capillary 15 can be connected or disconnected separately; the cap screws 6 (arranged in a larger circle than capillaries 15) can be easily tightened or loosened by an operator. Those skilled in the art will understand and appreciate that more or less than ten (10) ports may be used, and the size of the ports may be greater or less than 2 mm in diameter. The valve 1 of the present invention will be of advantage in the field of capillary chromatography and mass spectrometry. As used herein, the terms "capillary chromatographic system" and "capillary chromatography" shall be understood to refer to systems used for chromatographic analyses or mass spectrometry analyses performed thereon, and the like, which employ(s) one or more capillary columns. As used herein, "capillary column" means a capillary (capillary tube) having an outside diameter from about 50 to about 1600 microns. It will be understood that the capillaries which may be connected to the inventive valve need not be "capillary columns," although they may be. For example, some of the capillaries may be shorter capillaries which are used to feed or transfer fluids to a capillary column. Those skilled in the art will understand that the terms "chromatographic analysis" and "mass spectrometry analysis," and the like refer not only to the separation or partial separation of mixtures into their individual components, but also to methods in which a single, pure material is analyzed. In the latter situation, it may technically be the case that no "separation" occurs, because only a single, pure component is present. Further, as noted above a distinction is sometimes made between analytic methods which are performed for analytical purposes and those which are performed for preparative purposes. However, for convenience, the terms "chromatographic analysis" and "mass spectrometry analysis," and the like, as used herein will be understood to include separations and methods which are conducted for both analytical and preparative purposes.

Capillary chromatography has long been known for extremely high resolution, and it can be carried out using both gas and liquid mobile phases. In this sense the term "fluid" will be understood, as it normally is, to include both liquids and gases. The valve of the present invention is also useful in high pressure liquid chromatographic (HPLC) applications, including capillary HPLC. Thus, one embodiment of the invention is a capillary chromatographic system, including gas chromatographs and liquid chromatographs, comprising the valve of the invention.

In another embodiment of the invention, the capillary 15 are fused silica capillaries having an outside diameter of about 365 microns. In other embodiments, the outside diameter of the capillaries is between about 100 and 500 microns, and preferably between about 250 and 400 microns.

In yet another embodiment, the present invention is a method for carrying out a chromatographic mass spectrometry analysis, comprising: a) inserting one end of a capillary into an opening of a ferrule and the other end of the capillary through a clamp; b) placing a stator in contact with at least one of said ferrules, said stator having a stator front side and a stator flat surface opposite said front side, said stator front side having a plurality of impressions into which some or all of said ferrules are received, each of said impressions opening to a tube pocket, each of said impressions also having a stator through-hole opening onto said stator flat surface; c) disposing a plurality of capillary tubes through said ferrules into said tube pockets; d) applying pressure to said one or more ferrules; e) placing in contact with said stator a rotor comprising a stator-contact surface and a fluid communication channel such that said stator-contact surface abuts said stator flat surface and is rotatable about an axis to establish fluid communication between selected pairs of capillaries through said fluid communication channel; f) placing one or more of said capillaries in fluid communication with a capillary column; g) rotating said rotor to establish fluid communication between said capillary column and one or more of said capillaries; and h) passing a fluid through one or more of said capillaries and into said capillary column. In yet a further embodiment, the present invention is an automated method or automated chromatographic system or mass spectrometry for carrying out a chromatographic or mass spectrometry analysis using the valve of the invention.

In still another embodiment, the present invention is a method for connecting capillaries to a chromatographic or mass spectrometry system, the method comprising: a) providing a plurality of ferrules, each of said ferrules having a ferrule through-hole; b) disposing a plurality of capillary tubes through said ferrule through-holes; c) inserting the other end of each capillary through an opening in a clamp; and d) providing a plurality of impressions into which said some or all of ferrules are received, each of said impressions having a tube pocket into which one of said capillary tubes extends; and e) applying pressure to said one or more ferrule clusters.

While the present invention has been shown and described in its preferred embodiment and in certain specific alternative embodiments, those skilled in the art will recognize from the foregoing discussion that various changes, modifications, and variations may be made thereto without departing from the spirit and scope of the invention as set forth in the claims. Hence, the embodiment and specific dimensions, materials and the like are merely illustrative and do not limit the scope of the invention or the claims herein.

I claim:

1. A valve for capillary chromatography comprising:
   a housing having an interior chamber and having a first end with a plurality of openings;

a rotor located at least partially within the chamber of said housing, having a first end with a contact surface having at least one channel for fluid communication therein;

a stator located at least partially within the chamber of said housing, having first and second ends, with the first end having a plurality of impressions each adapted to hold a ferrule and a tube located within the ferrule, and with the second end of said stator abutting the first end of said rotor, and said stator having openings therethrough to allow fluid communication; and means located toward the outer edge of said housing for clamping the ferrule to said stator; and means for clamping each said ferrule to sealingly connect each said tube to an impression of the first end of said stator.

2. The valve according to claim 1 wherein the contact surface of said rotor comprises a plurality of channels therein.

3. The valve according to claim 1 wherein the contact surface of said rotor comprises glass.

4. The valve according to claim 1 wherein the contact surface of said rotor comprises quartz.

5. The valve according to claim 1 wherein the first end of said housing has at least five openings which form a substantially circular pattern.

6. The valve according to claim 1 wherein said valve comprises at least eight ports which form a substantially circular pattern.

7. The valve according to claim 1 wherein said housing comprises ten ports which form a substantially circular pattern which as a diameter of about six millimeters.

8. The valve according to claim 1 wherein the arcuate distance between the openings of said housing is about two millimeters.

9. The valve according to claim 1 wherein said clamping means comprises:

a clamp with an opening therethrough for holding a portion of a tube, and having threaded opening located at a selected distance from the opening for accepting a screw;

a screw engaged in the threaded opening to apply pressure to said clamp and hold said clamp against the first end of said stator.

10. A valve comprising:

a housing having an interior chamber and having a first end with a plurality of openings therethrough;

a rotor located at least partially within the chamber of said housing, having a first end with a contact surface having a plurality of channels etched therein for fluid communication;

a stator located at least partially within the chamber of said housing, having first and second ends, with the first end having a plurality of substantially conical impressions therein, each adapted to sealingly hold a ferrule and tube located within the ferrule, and with the second end of said stator abutting the first end of said rotor, and said stator having openings therethrough adapted to selectively allow fluid communication between said tube and at least one of the channels of said rotor;

a plurality of clamps, each having a first opening therethrough adapted to hold a tube located at a first end portion of each said clamp, and each further having second openings for engagement with a screw, with the opening located at a second end portion of each said clamp; and a plurality of screws, each located in a second opening of a corresponding one of said clamps; and wherein the first openings of said clamps are aligned with the openings of said housing.

11. The valve according to claim 10 further comprising:

at least eight openings in said housing;

at least eight clamps, with the first opening of each aligned with a corresponding one of said openings in said housing, and wherein the first openings of said clamps from a substantially circular pattern.

12. The valve according to claim 11 wherein the circular pattern has an approximate diameter of about ten millimeters or less.

13. A valve comprising:

a plurality of clamps, each having a first through-hole and a second through-hole;

a plurality of capillaries, each having a portion extending through at least one corresponding first through-hole of at least one of said clamps;

a plurality of ferrules, each having a through-hole in which at least a portion of a corresponding one of said capillaries is located, and each having a first end and a second end;

a stator having a first end in contact with the second end of said ferrules, and having a plurality of through-holes, each aligned with a corresponding one of the through-holes of said ferrules, and further having a second end;

a rotor having a first end abutting the second end of said stator and having a plurality of grooves therein, with the rotor being rotatable about an axis to selectively establish fluid communication between a plurality of said capillaries; and means for removably engaging said plurality of clamps to bias said ferrules against said stator.

14. The valve according to claim 13 further comprising:

a stator plate having a plurality of through-holes, and having a first end and a second end, and further having a seat adapted to receive one side of said plurality of clamps, wherein each of the through-holes of said stator plate are adapted to receive a screw extending through a corresponding one of said clamps.

15. The valve according to claim 14 further comprising:

a ferrule support having a plurality of through-holes arranged so that each of the through-holes of said ferrule support is aligned with a corresponding one of said ferrules.

16. The valve according to claim 15 wherein said valve comprises ten clamps, and the first through-holes of said clamps form a first substantially circular pattern with a diameter of about ten millimeters or less, and the second through-holes of said clamps form a second substantially circular pattern outside of the first substantially circular pattern.

17. The valve according to claim 16 wherein said rotor comprises zirconia.

18. The valve according to claim 16 wherein said stator comprises stainless steel.

19. The valve according to claim 16 wherein said ferrules comprise polyetherether ketone.

* * * * *